United States Patent
Fischell et al.

[11] Patent Number: 5,743,874
[45] Date of Patent: Apr. 28, 1998

[54] INTEGRATED CATHETER FOR BALLOON ANGIOPLASTY AND STENT DELIVERY

[76] Inventors: Robert E. Fischell, 14600 Viburnum Dr., Dayton, Md. 21036; David R. Fischell, 71 Riverlawn Dr., Fair Haven, N.J. 07704; Tim A. Fischell, 1018 Chancery La., Nashville, Tenn. 37215

[21] Appl. No.: 298,214

[22] Filed: Aug. 29, 1994

[51] Int. Cl.$^6$ .................................. A61M 29/00
[52] U.S. Cl. ........................ 604/96; 606/108; 606/194
[58] Field of Search ............................ 606/108, 194; 604/264, 280, 281, 96

[56] References Cited

U.S. PATENT DOCUMENTS

| | | | |
|---|---|---|---|
| 4,503,569 | 3/1985 | Dotter | 3/1.4 |
| 4,886,062 | 12/1989 | Wiktor | 606/194 |
| 4,969,458 | 11/1990 | Wiktor | 606/194 |
| 4,969,890 | 11/1990 | Sugita | 606/192 |
| 5,026,377 | 6/1991 | Burton et al. | 606/108 |
| 5,078,720 | 1/1992 | Burton et al. | 606/108 |
| 5,234,437 | 8/1993 | Sepetka | 606/108 |
| 5,266,073 | 11/1993 | Wall | 623/1 |
| 5,290,295 | 3/1994 | Querals et al. | 606/108 |
| 5,391,172 | 2/1995 | Williams et al. | 606/108 |

FOREIGN PATENT DOCUMENTS

| | | |
|---|---|---|
| 2102019 | 10/1993 | Canada . |
| 2111496 | 12/1993 | Canada . |
| 416662 | 7/1990 | European Pat. Off. . |
| 596145 | 10/1992 | European Pat. Off. . |
| 607468 | 12/1992 | European Pat. Off. . |
| 2617721 | 8/1988 | France . |
| 2255157 | 10/1990 | Japan . |

*Primary Examiner*—Corrine M. McDermott
*Attorney, Agent, or Firm*—Morton J. Rosenberg; David I. Klein; Jun Y. Lee

[57] ABSTRACT

A single, integrated catheter is capable of performing balloon angioplasty followed by delivery of a stent without removing the catheter from the patient's body. In one embodiment, a balloon placed near the catheter's distal end is first used for pre-dilatation of a vascular stenosis. The catheter is then advanced until a stent placed within a stent containment cavity located just proximal to the balloon is placed within the dilated stenosis. An outer sheath is then pulled back which allows a self-expanding stent to be deployed radially outward. The balloon is then pulled back inside the stent and reinflared to embed the stent into the dilated stenosis. An alternative embodiment of the invention uses a side opening in the catheter located just proximal to the stent containment cavity as an entry port for a flexible guide wire thus providing a "rapid exchange" capability for the integrated catheter.

15 Claims, 3 Drawing Sheets

5,743,874

1

INTEGRATED CATHETER FOR BALLOON ANGIOPLASTY AND STENT DELIVERY

FIELD OF USE

This invention is generally in the field of devices for opening vessels of the human body with specific application to percutaneous transluminal coronary angioplasty (PTCA) and stent delivery into the dilated artery.

BACKGROUND OF THE INVENTION

It is well known to use balloon angioplasty catheters for the dilatation of various vessels of the human body and most particularly for opening arteries. It is also well known to place stents into vessels to maintain patency of that vessel. It is also well known to use a balloon catheter for imbedding a stent into the wall of the vessel to prevent stent migration.

It is typical to use separate catheters for vessel dilatation and for stent delivery. This requires one or more catheter exchanges which increase the time and cost for performing interventional procedures. Since the patient is typically in some discomfort during such procedures, it is also highly advantageous to the patient to make the interventional procedure as short as possible.

SUMMARY OF THE INVENTION

The present invention overcomes the disadvantages of prior art devices by integrating a balloon catheter and a stent delivery catheter into a single device. Although this invention could be used for any vessel of the human body including but not limited to arteries, veins, vascular grafts, billiary ducts, urethras, fallopian tubes, bronchial tubes, etc., the descriptions herein will highlight the use of this device for arterial balloon angioplasty (and specifically PTCA) followed by intra-arterial stenting.

Thus an object of this invention is to perform vessel dilatation, stent placement, and balloon enhanced embedding of the stent into the vessel wall all with a single catheter.

Another object of this invention is to deploy a self-expanding stent by means of pulling back a slideable outer sheath thus allowing the stent to expand outwardly from a stent containment cavity located just proximal or distal to the expandable balloon which is located at or near the catheter's distal end.

Still another object of this invention is to have the integrated catheter capable of being advanced over a flexible guide wire.

These and other objects and advantages of this invention will become apparent to a person of ordinary skill in this art upon careful reading of the detailed description of this invention including the drawings as presented herein.

DETAILED DESCRIPTION OF THE INVENTION

A prior U.S. patent application (Ser. No. 08/273,459) by the same inventors (which is included herein by reference) describes various means for delivering self-expanding, shape memory metal stents into a vessel of the human body. The invention described herein expands the concepts taught in that prior application by including an expandable balloon located near the catheter's distal end whose purposes are to initially dilate a vessel and then, after a self-expanding stent is deployed, to further imbed that stent into the wall of the vessel.

Figure 1:
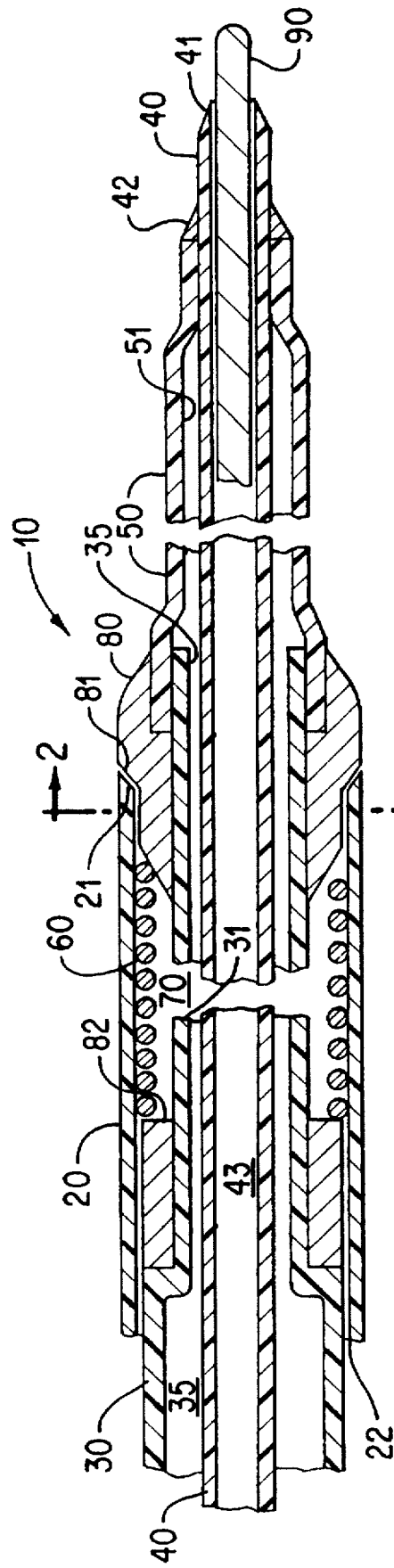
FIG. 1 is a longitudinal cross section of a distal portion of the integrated catheter.
Figure 2:
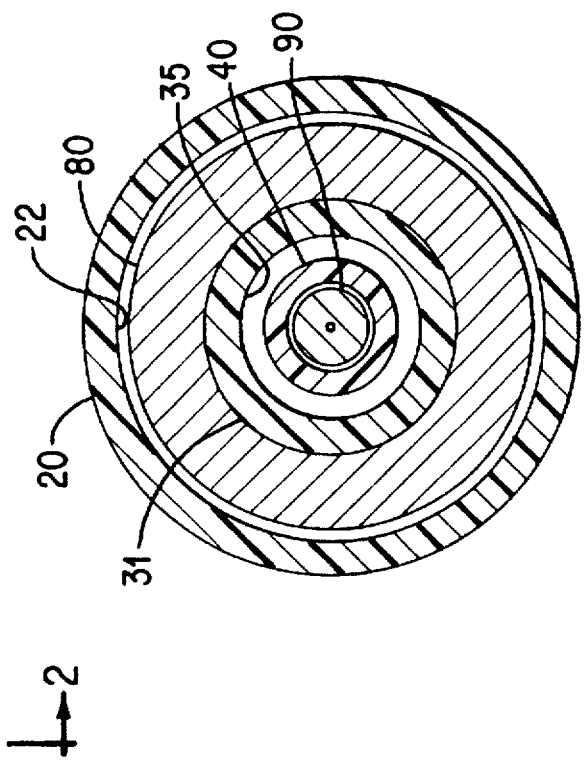
FIG. 2 is an enlarged transverse cross section of the catheter at section 2—2 of FIG. 1.
Figure 3:
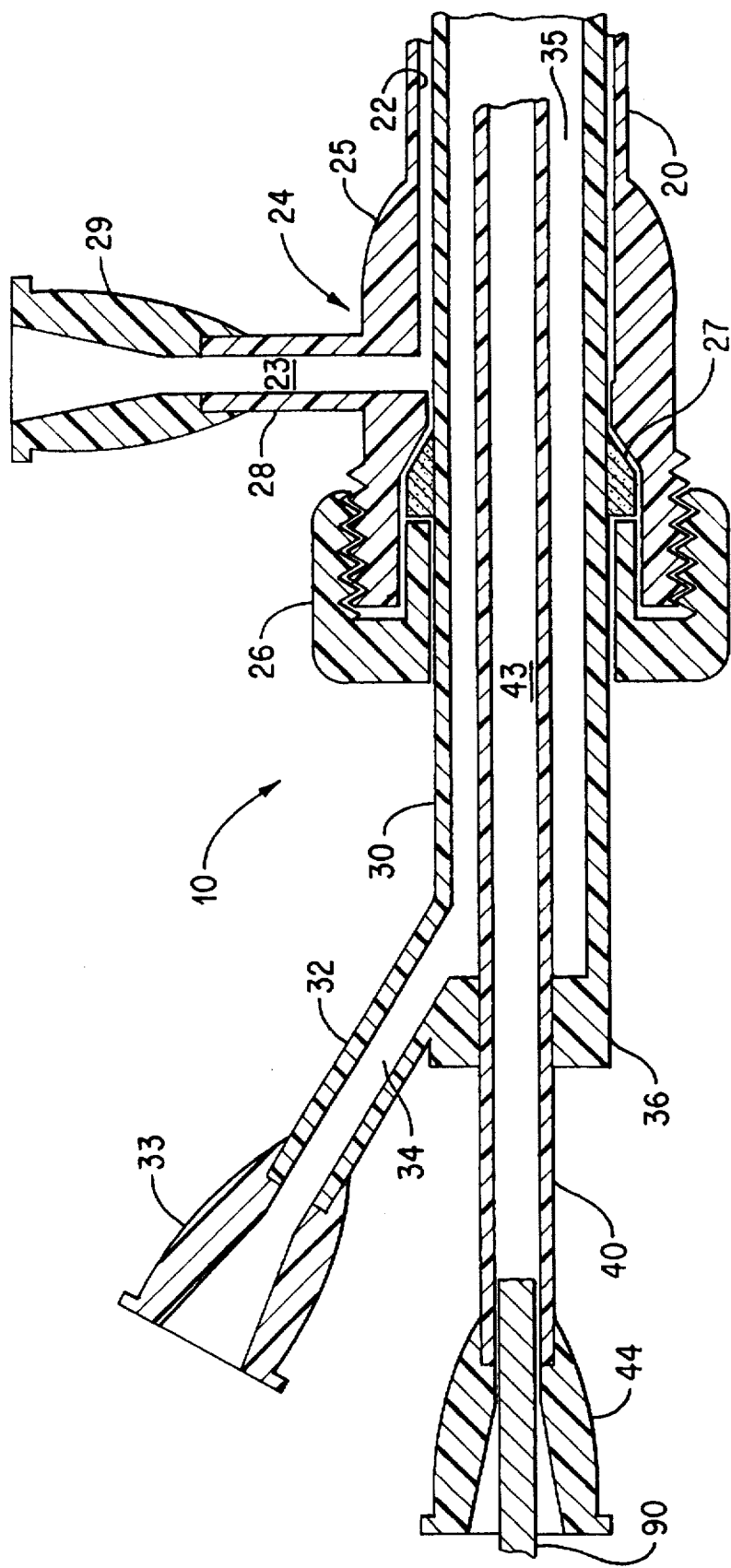
FIG. 3 is longitudinal cross section of a proximal portion of the integrated catheter illustrating means for guide wire and fluid access to various portions of the catheter.

FIGS. 1, 2 and 3 illustrate an integrated catheter 10 which includes a slideable outer sheath 20, an outer tube 30, an inner tuber 40, an expandable balloon 50, a stent 60 located in a stent containment cavity 70, and radiopaque marker bands 80 and 82.

The slideable outer sheath 20 has a tapered distal end 21 designed to join onto the conical surface 81 of the distal marker 80 thus forming a smooth and continuous outer surface for the distal portion of the catheter 10. At its proximal end, the sheath 20 is joined onto a Tuohy-Borst fitting 24 having a main body 25, a nut 26, a deformable elastomer gland 27 and a fluid delivery means consisting of a side arm 28 having a central lumen 23, the side arm 28 being joined at its proximal end to a female Luer fitting 29. The purpose of the fluid access means of the Tuohy-Borst fitting 24 is to flush the annular space 22 that lies between the sheath 20 and outer tube 30 (including the stent containment cavity 70) prior to placement of the catheter 10 into a vessel. By tightening down on the nut 26, the gland 27 seals the proximal end of the sheath 20 to prevent the escape of flushing fluid from the proximal end of the Tuohy-Borst fitting 24.

The outer tube 30 has a distal portion 31 that is adhesively bonded near its distal end to both the proximal end of the balloon 50 and distal marker band 80. The proximal end of the tube 30 has a side arm 32 and female Luer fitting 33 at the side arm's proximal end. The side arm 32 has a central lumen 34 which is in fluid communication with an annular passageway 35 that is formed between the inside surface of the outer tube 30 and outside surface of the inner tube 40. The proximal seal 36 of the tube 30 is bonded to the inner tube 40 to prevent fluid release when fluid is moved through the lumen 34 and passageway 35 to inflate or deflate the inside chamber 51 of the balloon 50. As seen in FIG. 1, adhesive 42 is typically used to join the distal end of the balloon 50 to the outer surface of the tube 40 near its tapered distal end 41. The integrated catheter 10 can really be any balloon angioplasty catheter to which stent delivery means has been added. The stent delivery means consists of the marker bands 80 and 82, the outer sheath 20 and the Tuohy-Borst fitting 24.

FIG. 3 shows that the female Luer fitting 44 is joined to the proximal end of the inner tube 40. A central lumen 43 extends throughout the entire length of the inner tube 40 including the Luer fitting 44. Either flushing fluid or a guide wire 90 can be placed through the Luer fitting 44, through the lumen 43 and out past the distal end 41 of the inner tube 40.

Referring now to FIG. 1, the proximal marker band 82 is adhesively joined to the proximal end of the distal portion 31 of the outer tube 30. The stent containment cavity 70 containing the self-expanding stent 60 is formed between the distal marker band 80, the proximal marker band 82, the inside surface of the outer sheath 20 and outside surface of the distal portion 31 of the outer tube 30.

The material(s) selected for the tubes 20, 30 and 40 can be Teflon or an elastomer such as polyurethane or polyethylene. The Tuohy-Borst fitting 24 is typically fabricated from a harder plastic such as PVC or Nylon or a higher durometer of the same elastomer used for the outer sheath 20. The length of the catheter 10 is typically 20 to 150 cm depending on the vessel into which it is to be used. The diameter of the catheter will typically vary from 1.0 to 10.0 mm depending on its use. The marker bands 80 and 82 are typically made from a dense metal such as an alloy of tantalum, platinum or gold.

A method for using the "over-the-wire" design, integrated catheter 10 for the treatment of an obstructed coronary artery would be as follows:

1. By conventional means, an introducer sheath and a coronary guiding catheter are inserted at the groin and the guiding catheter's distal end is advanced until it is situated within the ostium of a coronary artery.
2. Saline solution is flushed through each of the lumens and passageways of the catheter 10 by means of the three female Luer fittings 29, 33 and 44.
3. A guide wire 90 that has been pre-loaded into the integrated catheter 10 is advanced with the catheter 10 through the guiding catheter, and the guide wire 90 is then advanced through the coronary artery blockage.
4. The catheter 10 is further advanced over the guide wire 90 until the distal end 41 of the inner tube 40 lies distal to the blockage. This is accomplished with the outer sheath 20 in its most distal position (as shown in FIG. 1) and with the nut 26 of the Tuohy-Borst fitting 24 screwed down tightly to frictionally join the sheath 20 to the outer tube 30.
5. A fluid pressurization means is then joined to the Luer fitting 33 and the balloon 50 is inflated to an outside diameter between 2.0 and 5.0 mm depending on the nominal size of the coronary artery in which the blockage occurred.
6. The balloon 50 is then deflated and the catheter 10 is advanced until the stent 60 within the stent containment cavity 70 is situated within the dilated arterial blockage.
7. The nut 26 of the Tuohy-Borst fitting 24 is then loosened and the slideable outer sheath 20 is pulled back thus allowing the self-expanding stent 60 to expand radially outward.
8. The catheter 10 is then pulled back until the deflated balloon 50 lies within the expanded stent 60.
9. The balloon 50 is then reinflated, typically to a slightly higher pressure than was initially used for the arterial dilatation, thus further imbedding the stent into the arterial wall.
10. The balloon 50 is then deflated and the catheter 10 and the guide wire 90 are removed from the artery.
11. The guiding catheter and introducer sheath are then removed using appropriate methods that are well known in interventional cardiology.

As described in steps 1 through 11 above, a single integrated catheter 10 can be used for initial dilatation of a blockage in a vessel, for release of a stent within that vessel at the site where the dilatation occurred, and the balloon can be then reinflated to further imbed the stent into the wall of the vessel. Thus the requirement for one or more separate balloon dilatation catheters and a separate stent delivery catheter has been eliminated with a resulting cost economy and a decrease in the time required to perform this procedure.

Figure 4:
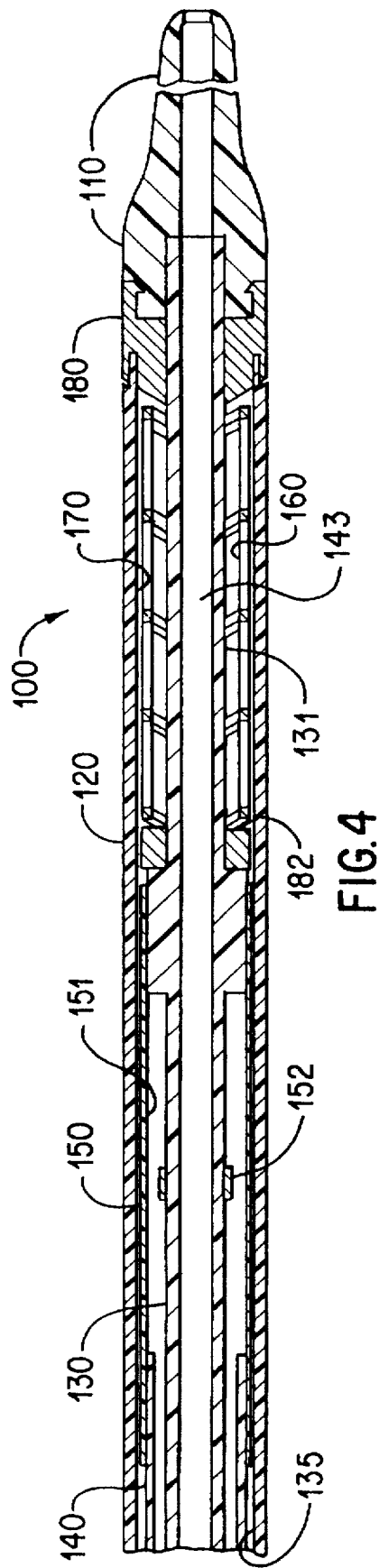
FIG. 4 is longitudinal cross section of a distal portion of an integrated catheter having the stent containment cavity distal to the balloon.

FIG. 4 illustrates an alternative embodiment of the "over-the-wire" integrated catheter in which the inflatable balloon is situated just proximal to the proximal end of the stent containment cavity. The integrated catheter 100 of FIG. 4 has a flexible tip 110, a slideable outer sheath 120, an inner tube 130 having a central through lumen 143, an outer tube 140, and an inflatable balloon 150 having an interior chamber 151 which has a radiopaque band 152 at its center. A self-expanding stent 160 is enclosed within a stent containment cavity 170 that lies between the inside surface of the outer sheath 120, the outside surface of the distal segment 131 of the inner tube 130, the proximal radiopaque marker 182 and the distal radiopaque marker 180. The proximal end of the catheter 100 would be essentially the same design as shown in FIG. 3. Fluid to inflate and deflate the balloon 150 would pass through the annular passageway 135 (equivalent to the passageway 35 shown in FIG. 3) which is in fluid communication with the balloon's interior chamber 151 which is equivalent to the interior chamber 51 of the catheter 10 of FIG. 1.

The design of FIG. 4 would operate as follows:

1. Angioplasty or atherectomy would be conducted in the obstructed artery.
2. The angioplasty or atherectomy catheter would then be removed and the integrated catheter 100 of FIG. 4 would be advanced over a guide wire (not shown) until the stent containment cavity 170 is situated at the site where the artery opening procedure was performed.
3. The outer sheath 120 is then pulled back until its distal end lies proximal to the proximal end of the balloon 150 thus releasing the self-expanding stent.
4. The catheter 100 is then advanced until the balloon 150 is situated within the expanded stent 160 and then the balloon 150 is inflated.
5. The balloon 150 is then deflated and the catheter 100 is removed from the body.

Although the catheter 100 does not have the advantage of being able to perform balloon angioplasty, it does save one exchange in that it carries a balloon that can be used for imbedding the stent into the arterial wall.

It is also envisioned to place the balloon at the bottom of the stent containment cavity instead of either distal or proximal to the stent containment cavity. This design is a simple variation of the design of FIG. 4.

Figure 5:
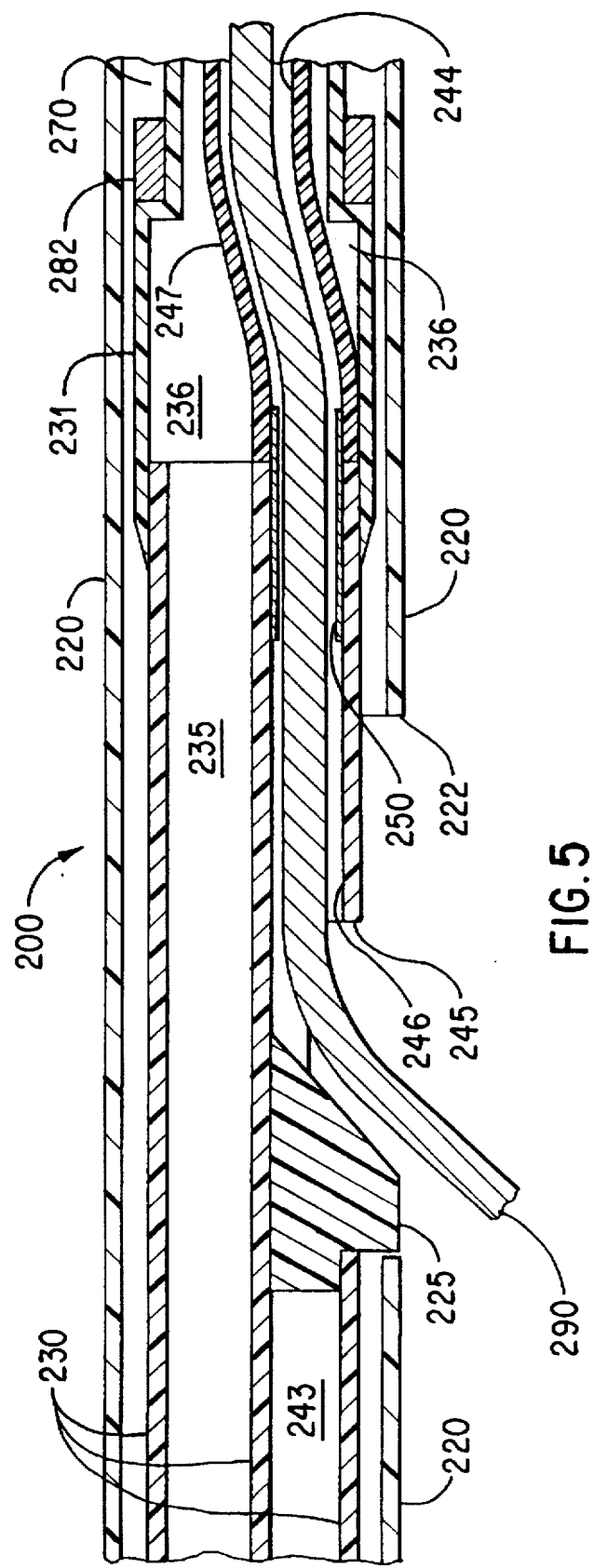
FIG. 5 is a longitudinal cross section of a portion of an integrated catheter having a guide wire that exits the catheter within the distal half-length of the catheter.

Another alternative embodiment that utilizes a "rapid-exchange" concept for the integrated catheter is shown in FIG. 5. Although the operation of such an integrated catheter is described in U.S. patent application Ser. No. 08/273,459 which has been included herein by reference, the basic elements of this design will also be described in this specification.

FIG. 5 shows a longitudinal cross section of a portion of the "rapid-exchange" (as opposed to "over-the wire") integrated catheter 200 which portion is located just proximal to a stent containment cavity 270. The catheter 200 has an outer sheath 220 having a side opening 222 through which a guide wire 290 can pass, and a dual lumen tube 230 having a balloon inflate/deflate lumen 235 and a second lumen 243 which is blocked at its distal end by the plug 225 and a single radiopaque marker band 282. The distal end of the lumen 235 enters into an annular passageway 236 which is in fluid communication with the interior of an inflatable angioplasty balloon as illustrated in FIG. 1. The dual lumen tube 230 is joined at its distal end to the proximal end of the outer cylindrical tube 231 which encloses the annular passageway 236. A thin-walled steel tube 250 is inserted into the distal end of the lumen 246 at the distal end of the dual lumen tube 230. The tube 250 forms a fluid tight connection between the distal end of the lumen 246 and the proximal end of the guide wire lumen 244. An opening 245 allows the guide wire 290 to exit from the proximal end of the lumen 246.

As previously illustrated in FIG. 1, the distal end of the tube 231 can join to the proximal end of an angioplasty balloon, and the cylindrical tube 247 can be joined near its distal end to the distal end of an angioplasty balloon. The guide wire 290 would emerge into an artery from the distal end of the tube 247 also as illustrated in FIG. 1.

The fluid entry means at the proximal end of "rapid-exchange" type catheter designs is well known in the art of balloon angioplasty catheters. The method for joining the proximal end of the outer sheath 220 to the exterior surface of the dual lumen tube 230 by means of a Tuohy-Borst fitting is illustrated in FIG. 3. Thus, a "rapid-exchange" type integrated catheter 200 is clearly an achievable design.

It should also be understood that the invention described herein can be used with a variety of angioplasty balloon catheters including those with fixed guide wires at their distal end.

It should be further understood that one, two or more radiopaque markers could be used with any integrated design.

Additional objects and advantages of the present invention will become apparent to those skilled in the art to which this invention relates from the subsequent description of the preferred embodiments and the appended claims, taken in conjunction with the accompanying drawings.

What is claimed is:

1. An integrated catheter for performing a dilatation procedure within a vessel of a human body and for placement of a stent within that region of the vessel that underwent dilatation, the catheter comprising:

a balloon angioplasty center in the form of an elongated tubular member having a proximal end and a distal end and having a non-extensible inflatable balloon and longitudinal length of decreased diameter forming a stent containment cavity both located near the tubular member's distal end;

a self-expanding stent initially located within the stent containment cavity, the stent being operational to automatically expand radially outward at the normal temperature of the human body, the stent containment cavity having a proximal end and a distal end and the balloon having a proximal end and a distal end, the distal end and proximal end of the stent containment cavity each being defined by a surface that extends generally radially outward from the surface of the elongated tubular member;

a slideable outer sheath coaxially placed over the elongated tubular member and adapted to retain the self-expanding stent in its unexpanded state when the outer sheath is advanced to a forward, distal position thus forming a cover over the stent containment cavity, the outer sheath extending distally at least to the radially outward extending surface that defines the stent containment cavity's distal end, and the outer sheath having a proximal pullback means lying outside the human body for pulling the sheath back in a proximal direction to a proximal position so as to uncover the stent containment cavity thus allowing the stent to expand radially outward against the vessel wall, whereby when the sheath is displaced for deployment of said stent a distal end of said slideable outer sheath is positioned proximal said stent; and, a radiopaque marker band having a proximal surface is located at a stent containment cavity distal end, said proximal surface defining the distal end of said stent containment cavity.

2. The catheter of claim 1 wherein the stent containment cavity is situated just proximal to the proximal end of the inflatable balloon.

3. The catheter of claim 1 wherein the stent containment cavity is situated near the tubular member's distal end and the inflatable balloon is situated just proximal to the proximal end of the stent containment cavity.

4. The catheter of claim 1 wherein the elongated tubular member of the balloon angioplasty catheter has a central lumen throughout its entire length through which a flexible guide wire can be slideably advanced, that is, the balloon angioplasty catheter is of the "over-the-wire" design.

5. The catheter of claim 1 wherein the elongated tubular member of the balloon angioplasty catheter has a proximal half-length and a distal half-length and includes a side opening located in the distal half-length, the catheter being a "rapid-exchange" design that allows a guide wire to exit from the side opening located within the distal half-length of the elongated tubular member.

6. The catheter of claim 1 wherein the self-expanding stent is made from a shape memory alloy.

7. The catheter of claim 6 wherein the shape memory alloy is Nitinol.

8. The catheter of claim 1 wherein the proximal pullback means is a Tuohy-Borst fitting.

9. The catheter of claim 1 wherein a further radiopaque marker band is located at the proximal end of the stent containment cavity.

10. A rapid exchange integrated catheter for performing a dilatation procedure within a vessel of a human body and for placement of a stent within that region of the vessel that underwent dilatation, the cather comprising:

a balloon angioplasty catheter in the form of an elongated tubular member having a proximal end and a distal end and having an inflatable balloon and a longitudinal length of decreased diameter forming a stent containment cavity both located near the tubular member's distal end;

a self-expanding stent initially located within the stent containment cavity, the stent containment cavity having a proximal end and a distal end and the balloon having a proximal end and a distal end, the distal end and proximal end of the stent containment cavity each being defined by a surface that extends generally radially outward from the surface of the elongated tubular member;

a radiopaque marker band having a proximal surface located adjacent said stent containment cavity distal end, said radiopaque marker band proximal surface defining the distal end of said stent containment cavity; and, an outer sheath slideably and coaxially situated around the elongated tubular member, the outer sheath being adapted to retain the self-expanding stent in its unexpanded state when the outer sheath is advanced to a forward, distal position thus forming a cover over the stent containment cavity, the outer sheath having a proximal pullback means lying outside the human body for pulling the sheath back to a proximal position so as to uncover the stent containment cavity thus allowing the stent to expand radially outward against the vessel wall, and the outer sheath also having a side opening situated just proximal to the proximal end of the stent containment cavity, the side opening being adapted to pass a flexible guide wire therethrough.

11. The catheter of claim 10 wherein the stent containment cavity is situated just proximal to the proximal end of the inflatable balloon.

12. The catheter of claim 10 wherein the stent containment cavity is situated near the tubular member's distal end and the inflatable balloon is situated just proximal to the proximal end of the stent containment cavity.

13. The catheter of claim 10 wherein a further radiopaque marker band is located at the proximal end of the stent containment cavity.

14. A method for performing balloon angioplasty followed by stent placement within a vessel of a human body, the method comprising the following steps:

(a) inserting an integrated catheter including an elongated tubular member, said integrated catheter further including a distal end and which has an inflatable balloon and a stent containment cavity both located near the catheter's distal end into the vessel of a human body, the stent containment cavity containing a self-expanding stent and having a distal end and a proximal end and a radiopaque marker band situated at the stent containment cavity's distal end, wherein an outer sheath is coaxially placed on said elongated tubular member;

(b) performing balloon angioplasty at a site in the vessel;

(c) deflating the balloon and advancing the catheter until the stent containment cavity's distal end lies just distal to the site of the dilatation; and (d) pulling back the outer sheath thus allowing the self-expanding stent to automatically deploy at the site of the dilatation.

15. The method of claim 14 further comprising the step of (a) pulling back on the integrated catheter so that the balloon lies within the deployed stent; and (b) reinflating the balloon so as to further imbed the stent into the vessel wall.

\* \* \* \* \*